(12) United States Patent
Clark (10) Patent No.: US 8,393,897 B2
(45) Date of Patent: Mar. 12, 2013

(54) METHODS AND DEVICES FOR DIASTEMA CLOSURE

(76) Inventor: David J. Clark, Lakewood, WA (US)

( * ) Notice: Subject to any disclaimer, the term of this patent is extended or adjusted under 35 U.S.C. 154(b) by 122 days.

(21) Appl. No.: 12/267,539

(22) Filed: Nov. 7, 2008

(65) Prior Publication Data

US 2009/0208896 A1 Aug. 20, 2009

Related U.S. Application Data (60) Provisional application No. 60/986,244, filed on Nov. 7, 2007.

(51) Int. Cl.
*A61C 5/04* (2006.01)
(52) U.S. Cl. .............................................. 433/39
(58) Field of Classification Search .................. 433/39, 433/40, 126
See application file for complete search history.

(56) References Cited

U.S. PATENT DOCUMENTS

| | | | |
|---|---|---|---|
| 2,611,182 A | 9/1952 | Tofflemire | |
| 2,674,801 A * | 4/1954 | Trangmar | 433/39 |
| 3,108,377 A | 10/1963 | Meyer | |
| 3,842,505 A * | 10/1974 | Eames | 433/39 |
| 4,024,643 A | 5/1977 | Eisenberg | |
| 4,259,070 A | 3/1981 | Soelberg et al. | |
| 4,337,041 A | 6/1982 | Harsany | |
| 4,449,928 A * | 5/1984 | von Weissenfluh | 433/40 |
| 4,468,199 A | 8/1984 | Weikel | |
| 4,523,909 A | 6/1985 | Lazarus | |
| 4,536,155 A | 8/1985 | Ireland | |
| 4,553,937 A | 11/1985 | Ropers | |
| 4,601,662 A | 7/1986 | Galler | |
| 4,704,087 A * | 11/1987 | Dragan | 433/39 |
| 4,718,849 A * | 1/1988 | von Weissenfluh et al. | 433/39 |
| 4,781,583 A | 11/1988 | Lazarus | |
| 4,997,367 A | 3/1991 | Kassel | |
| 5,017,140 A | 5/1991 | Ascher | |
| 5,104,317 A | 4/1992 | Riazi | |
| 5,114,341 A * | 5/1992 | Kassel | 433/39 |
| 5,425,635 A | 6/1995 | Croll | |
| 5,460,525 A | 10/1995 | Rashid | |
| 5,501,595 A | 3/1996 | Brorson | |
| 5,527,181 A | 6/1996 | Rawls et al. | |
| 5,607,302 A | 3/1997 | Garrison et al. | |
| 5,622,496 A | 4/1997 | Champagne | |
| 5,626,476 A | 5/1997 | Champagne | |
| 5,730,592 A | 3/1998 | Meyer | |

(Continued)

FOREIGN PATENT DOCUMENTS

EP 0 087 022 * 8/1983

*Primary Examiner* — Ralph Lewis
(74) *Attorney, Agent, or Firm* — Quarles & Brady LLP (57) ABSTRACT

In a method for closing a diastema and/or papilla regeneration between a first tooth and a second tooth, a dental matrix is used. The dental matrix includes a curved sectional strip of material. The strip has a length from a first end to a second end sufficient to create a form for molding a restorative material to a surface of the first tooth. The strip has a root end section and a second section integral with the root end section. The root end section of the strip is anatomic in shape such that the root end section hugs the gingival portion of the first tooth. In one form, a non-anatomic bulge is formed in the second section. The root end section of the matrix can slide to the depth of the sulcus without lacerating the tissue. After inserting the root end section of the dental matrix into the sulcus between the papilla and the gingival portion of the first tooth, a composite restorative material is placed between the dental matrix and a cervical surface of the first tooth. The composite restorative material is then cured. This creates bulbousness in the cured composite near the gum line to fill the gingival gapping.

18 Claims, 7 Drawing Sheets

U.S. PATENT DOCUMENTS

| | | |
|---|---|---|
| 5,807,101 A | 9/1998 | Scalzo |
| 5,975,906 A | 11/1999 | Knutson |
| 5,997,302 A | 12/1999 | Alpert |
| 6,079,978 A | 6/2000 | Kunkel |
| 6,142,778 A | 11/2000 | Summer |
| 6,155,823 A | 12/2000 | Nagel |
| 6,162,055 A | 12/2000 | Montgomery et al. |
| D439,667 S | 3/2001 | Brown |
| 6,206,697 B1 | 3/2001 | Hugo |
| 6,234,793 B1 | 5/2001 | Brattesani et al. |
| 6,315,566 B1 | 11/2001 | Shen et al. |
| 6,325,625 B1 | 12/2001 | Meyer |
| 6,350,122 B1 | 2/2002 | Meyer |
| 6,425,760 B1 | 7/2002 | Summer et al. |
| 6,435,874 B1 | 8/2002 | Hughes |
| 6,479,592 B2 | 11/2002 | Rheinberger et al. |
| 6,482,007 B2 | 11/2002 | Stanwich et al. |
| 6,540,072 B1 | 4/2003 | Fischer |
| 6,619,956 B1 | 9/2003 | Weir |
| 6,712,608 B2 * | 3/2004 | Bills .................... 433/39 |
| 6,893,258 B1 | 5/2005 | Kert |
| 2002/0119424 A1 | 8/2002 | Margeas et al. |
| 2002/0128347 A1 | 9/2002 | Blackwell et al. |
| 2003/0069326 A1 | 4/2003 | Stangel et al. |
| 2003/0165793 A1 | 9/2003 | Yobel et al. |
| 2004/0053189 A1 | 3/2004 | Friedman |
| 2004/0229186 A1 | 11/2004 | Slone |
| 2005/0074716 A1 | 4/2005 | Cleary et al. |
| 2005/0089813 A1 * | 4/2005 | Slone .................... 433/39 |
| 2005/0231983 A1 | 10/2005 | Dahm |
| 2005/0255428 A1 | 11/2005 | Coopersmith |
| 2005/0287490 A1 | 12/2005 | Stookey et al. |
| 2005/0287491 A1 | 12/2005 | Slone |
| 2006/0009540 A1 | 1/2006 | Jia et al. |
| 2006/0019217 A1 | 1/2006 | Yates |
| 2006/0084029 A1 | 4/2006 | Viscomi et al. |
| 2006/0088798 A1 | 4/2006 | Feinbloom et al. |
| 2006/0110700 A1 | 5/2006 | Cipolla et al. |
| 2006/0154197 A1 | 7/2006 | Gargiulo |
| 2006/0155171 A1 | 7/2006 | Yang |
| 2006/0188835 A1 | 8/2006 | Nagel et al. |
| 2006/0275732 A1 | 12/2006 | Cao |
| 2006/0275733 A1 | 12/2006 | Cao |
| 2008/0064000 A1 | 3/2008 | Clark |
| 2008/0064002 A1 | 3/2008 | Clark |
| 2008/0064003 A1 | 3/2008 | Clark |
| 2008/0064004 A1 | 3/2008 | Clark |
| 2008/0064009 A1 | 3/2008 | Clark |
| 2008/0064012 A1 | 3/2008 | Clark |
| 2009/0029324 A1 | 1/2009 | Clark |

* cited by examiner

METHODS AND DEVICES FOR DIASTEMA CLOSURE

CROSS-REFERENCES TO RELATED APPLICATIONS

This application claims priority from U.S. Provisional Patent Application No. 60/986,244 filed Nov. 7, 2007.

STATEMENT REGARDING FEDERALLY SPONSORED RESEARCH

Not Applicable.

BACKGROUND OF THE INVENTION

1. Field of the Invention

This invention relates to methods and devices for diastema closure and/or papilla regeneration.

2. Description of the Related Art

Gaps or "diastemas" can be present between the teeth for a variety of reasons. These include genetic and ethnic trends where there is a tooth-jaw discrepancy wherein the teeth are too small for the jaws or jaws too large for the tooth size. It is also common for the gums to recede over time creating dark triangles or spaces referred to as gingival diastemas. In the modern era of cosmetically aware patients, dentists are often asked to close small and large diastemas. Patients also ask to treat the black triangle (loss or shrinkage of the interdental papilla) by restorative or microsurgical techniques.

It is common to treat the gapping by filling the space with a bonded porcelain veneer; fabricated in most instances in a dental laboratory and then later bonded to the affected teeth. It is also very common and more expedient to close the diastemas with direct filling materials, namely bonded composite resin. In the past, a flat plastic strip (such as a Mylar™ strip) was placed and often adapted to the tooth with an interdental wedge or elastic spacer. There have been problems with all previous techniques.

In previous clinician option 1, no matrix is used. In severe diastema cases, the clinician sometimes uses the papilla (gum triangle) itself as a gingival matrix. This resulted in a good esthetic space closure, but often a biologically horrific contour. A sharp 90° angle combined with a lumpy and porous surface creates a poor environment for soft-tissue health.

In previous clinician option 2, a matrix is used with an interdental wedge. The problems with traditional clear plastic strips are that they are flat and require wedging, do not conform to the tooth, and are nearly impossible to maintain deep in the sulcus. The result is often an esthetic compromise. Furthermore, holding all four ends of the plastic strips while simultaneously light-curing a composite filling is always a challenge.

In previous clinician option 3, a matrix is used without a wedge. This approach can yield the worst of both worlds, incomplete space closure and gingival overhang. The flat plastic strip will not allow the required bulbousness near the gum line to fill the gingival gapping. Because the stock (flat) plastic strip does adapt in a facial-palatal direction, it will not stay in the sulcus and therefore wanders away from intimate adaptation to the rounded root, leaving the shelf or "overhang" that creates poor gingival health and shredding of floss, odor and food impaction.

Thus, there is a need for improved methods and devices for diastema closure and/or papilla regeneration.

SUMMARY OF THE INVENTION

The foregoing needs are met by the invention which provides methods and devices for diastema closure and/or papilla regeneration.

In one aspect, the invention provides a dental matrix for diastema closure and/or papilla regeneration. The matrix includes a curved strip of material. The strip has a length from a first end to a second end sufficient to create a form for molding a restorative material to a surface of a tooth being restored. The strip has a root end section and a second section integral with the root end section wherein the root end section of the strip is anatomic in shape. The root end section can be dimensioned such that the root end section can engage papilla and a gingival portion of the tooth when the root end section is inserted into the sulcus between the papilla and the gingival portion of the tooth.

The second section of the matrix can extend outwardly away from a root-crown junction of the root end section and the second section. A curved profile can be formed in the second section adjacent the root-crown junction. In one form, a non-anatomic bulge is formed in the second section. The root end section can have a vertical dimension in the range of 0.5 to 2 millimeters. The dental matrix can comprise a translucent material. In one version, the strip includes a third section integral with the second section wherein the root end section and the third section are on opposite sides of the second section. The root end section and/or the third section of the strip can be tooth specific. The root end section and/or the third section of the strip can be specific to an anterior tooth. The root end section and/or the third section of the strip can be tooth type specific. The root end section and/or the third section of the strip can be tooth surface specific. The strip of the dental matrix can be dimensioned such that the dental matrix is suitable for use without an interdental wedge or an elastic separator or a spacer.

In another aspect of the invention, there is provided a method for closing a diastema between a first tooth and a second tooth. The method can use a dental matrix according to the invention as summarized above. The root end section of the dental matrix is inserted into the sulcus between the papilla and the gingival portion of the first tooth. A composite restorative material is placed between the dental matrix and a cervical surface of the first tooth, and then the composite restorative material is cured. A surface of the cured composite restorative material bonded to the cervical surface of the first tooth can be curved. A second composite restorative material can be placed between the dental matrix and an interproximal surface of the first tooth and thereafter cured. The method can use a second dental matrix according to the invention as summarized above. The root end section of the second dental matrix is inserted into the sulcus between the papilla and the gingival portion of the second tooth. A second composite restorative material is placed between the second dental matrix and a cervical surface of the second tooth. The second composite restorative material is then cured.

In still another aspect, the invention provides a method for regenerating papilla between a first tooth and a second tooth. The method can use a dental matrix according to the invention as summarized above. The root end section of the dental matrix is inserted into the sulcus between the papilla and the gingival portion of the first tooth. A composite restorative material is placed between the dental matrix and a cervical surface of the first tooth. The composite restorative material is then cured. A surface of the cured composite restorative material bonded to the cervical surface of the first tooth can be curved. The method can use a second dental matrix according to the invention as summarized above. The root end section of the second dental matrix is inserted into the sulcus between the papilla and the gingival portion of the second tooth. A second composite restorative material is placed between the second dental matrix and a cervical surface of the second tooth, and the second composite restorative material is then cured.

It is an advantage of the present invention to provide methods and devices for diastema closure and/or papilla regeneration that provide rounded marginal profiles.

It is another advantage of the present invention to provide methods and devices for diastema closure and/or papilla regeneration that do not compromise the root-crown architecture.

It is yet another advantage of the present invention to provide methods and devices for diastema closure and/or papilla regeneration that provide for bulbousness near the gum line to fill the gingival gapping.

It is still another advantage of the present invention to provide a matrix for diastema closure and/or papilla regeneration wherein the matrix has an anatomic shape in the gingival portion but then with varying levels of exaggerated profile at the root-crown junction.

It is yet another advantage of the present invention to provide a matrix for diastema closure and/or papilla regeneration wherein the matrix is a sectional matrix that is specific to the anterior teeth and specifically designed for diastema closure with bonded composite filling material.

It is still another advantage of the present invention to provide a matrix for diastema closure and/or papilla regeneration wherein the matrix is a matrix specifically designed for the closure of diastema (tooth gapping).

It is yet another advantage of the present invention to provide a matrix for diastema closure and/or papilla regeneration wherein the matrix is a sectional matrix that is tooth specific with an exaggerated root-crown profile.

It is still another advantage of the present invention to provide a matrix for diastema closure and/or papilla regeneration wherein the matrix is a sectional matrix that is tooth and surface specific with an exaggerated root-crown profile.

It is yet another advantage of the present invention to provide devices for diastema closure and/or papilla regeneration with precise fit of custom matrices that allows the matrices to be used without interdental wedges or elastic separators or spacers.

It is still another advantage of the present invention to provide methods and devices for diastema closure and/or papilla regeneration that allow for formation of aesthetically pleasing papilla between adjacent teeth after diastema closure.

It is yet another advantage of the present invention to provide methods and devices for diastema closure and/or papilla regeneration that avoid subsequent deterioration in periodontal health after diastema closure.

It is still another advantage of the present invention to provide a matrix for diastema closure and/or papilla regeneration wherein the matrix can slide to the depth of the sulcus without lacerating the tissue.

These and other features, aspects, and advantages of the present invention will become better understood upon consideration of the following detailed description, drawings and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

In one example method according to the invention for closing a diastema, the dentist first locates a diastema needing closure. Optionally, the dentist may remove any portion of either of the teeth adjacent the diastema. This can involve the removal of old composite. Then, the gingiva can be lightly sculpted to create space for a sectional matrix according to the invention. This sculpting can be accomplished with a mini tip and electrosurgery, laser, or sodium bicarbonate spray, which can be used to simultaneously sculpt tissue and clean and detoxify any sickly cementoenamel junction surfaces.

Figure 1:
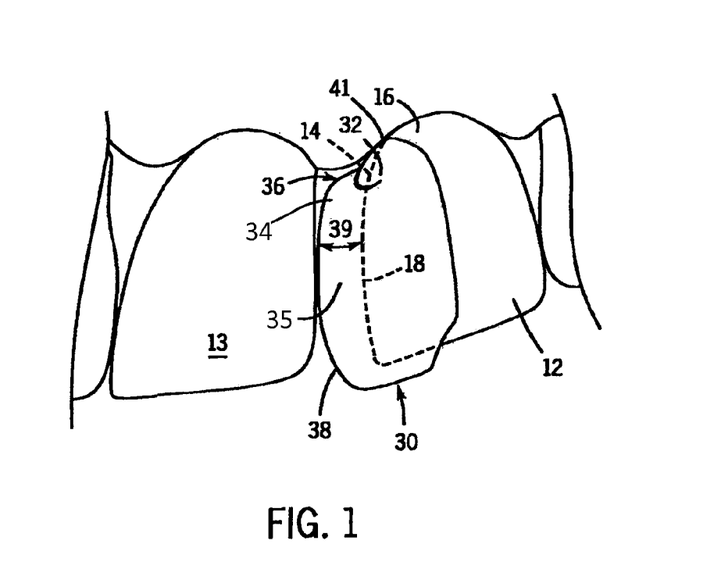
FIG. 1 is a front view of human teeth showing an upper incisor having a dental matrix according to the invention placed on the incisor.

Turning first to FIG. 1, various dental matrices according to the invention that are suitable for closing a diastema using the method of the invention are shown. In FIG. 1, an upper incisor 12 having a clear sectional dental matrix 30 placed on the incisor 12 is shown. The dental matrix 30 can be formed from a translucent or transparent material such as a polymeric film. One non-limiting example material is the polyester film commercially available as Mylar™. However, metallic (stiff) materials can be used for the matrix 30. Also, the matrix 30 may have variable thickness. The matrix has a strip of material having a length from a first end to a second end sufficient to create a form for molding a restorative material to a surface of a tooth being restored. The length of the strip can surround 90 to 370 degrees of the tooth.

The matrix 30 has a first root end section 32 that is anatomic in shape. The actual anatomic shapes of the root end section 32 of the matrix 30 can be created from scans of natural teeth, molds of natural teeth, and/or molds of tooth models. Thus, by "anatomic", it is meant that the root end section 32 of the matrix 30 has an inner surface that conforms to the shape of the outer surface of a particular region of the natural tooth that contacts the root end section 32 of the matrix 30. In FIG. 1, the root end section 32 of the matrix 30 conforms to the outer surface 14 of the gingival portion 16 of the tooth 12. The root end section 32 of the matrix 30 can be fully or partially anatomic. As a result, the matrix 30 can be used without interdental wedges or elastic separators or spacers. The anatomic shape allows hands-free and wedge-free use as the matrix 30 hugs the tooth 12. The root end section can have a vertical dimension in the range of 0.5 to 2 millimeters.

The sectional matrix 30 has a second (crown root junction profile) section 34 that is integral with the root end section 32. The second section 34 is not anatomically shaped to conform to the shape of the outer surface 18 of the tooth 12. The outer surface 18 may have been created by removal of portions of the tooth 12. Looking at FIG. 1, an exaggerated root-crown profile 36 of the second section 34 is created at the junction of the root end section 32 and the second section 34. The exaggerated root-crown profile 36 extends away from the outer surface 18 of the tooth 12. The exaggerated root-crown profile 36 merges with a side profile 38 of the second section 34 of the matrix 30. The exaggerated root-crown profile 36 and the side profile 38 of the second section 34 of the matrix 30 create a mild to severe non-anatomic bulge. The space 39 between the outer surface 18 of the tooth 12 and the inner surface of the exaggerated root-crown profile 36 and the side profile 38 creates a mold for the dental filling material that closes the diastema between tooth 12 and tooth 13. The sectional matrix 30 also has a third (incisal) section 35 that is integral with the second section 34. The third section 35 of the matrix 30 can be fully or partially anatomic. The third section 35 of the matrix 30 may comprise about the bottom half of the matrix 30.

The root end section 32 and the third section 35 of the matrix 30 can be tooth specific. By "tooth specific" it is meant that the root end section 32 and the third section 35 of the matrix 30 are configured to conform to the shape of the outer surface of the specific natural tooth being restored, such as (without limitation) a maxillary lateral incisor. The root end section 32 and the third section 35 of the matrix 30 can also be tooth type specific. By "tooth type specific" it is meant that the root end section 32 and the third section 35 of the matrix 30 are configured to conform to the shape of the outer surface of the specific type of natural tooth such as (without limitation) an incisor. The root end section 32 and the third section 35 of the matrix 30 can be tooth surface specific. By "tooth surface specific" it is meant that the root end section 32 and the third section 35 of the matrix 30 are configured to conform to the shape of the outer surface of the specific natural tooth surface such (without limitation) a lingual or buccal incisor surface.

Still looking at FIG. 1, the clear plastic anatomical sectional matrix 30 is placed around the tooth 12 and maintains anatomic root adaptation contact by way of the anatomic root end section 32 of the matrix 30. The matrix 30 is self wedging and self stabilizing. The outer surface 18 of tooth 12 is then etched with liquid and/or gel phosphoric acid. Alternatively, the method can incorporate self etching resins that do not require a separate etching step with phosphoric acid; or any technique that allows a filling material to bond to dentin (cementum) and enamel. The outer surface 18 of tooth 12 can be reached by way of a slit in the end 41 of the matrix 30, or by gently pulling the incisal portion of the matrix 30 away from the tooth while leaving the gingival portion of the matrix 30 undisturbed. The outer surface 18 of tooth 12 is then rinsed and dried. A lightly filled or unfilled light curable resin tooth bonding agent is then applied to outer surface 18 of tooth 12. The resin tooth bonding agent is not light cured at this point. Resin tooth bonding agents improve composite to enamel and/or dentin bonding. However, a resin bonding agent may not be required. One example resin tooth bonding agent is available under the tradename OptiBond Solo Plus®.

A light curable flowable composite resin is then injected directly on the resin tooth bonding agent (under magnification if possible) without incorporating bubbles. A tiny amount of the light curable flowable composite resin is expressed before placement to ensure that there is no air in the cannula. The light curable flowable composite and resin tooth bonding agent are not light cured at this point. Generally, light curable flowable composite resins contain 20-25 percent less filler in the light curable polymeric material than nonflowable paste materials. Light curable flowable composite resins are available under tradenames such as Filtek™, Flow-It™, EsthetX®, Revolution®, AeliteFlo®, PermaFlo®, Dyract Flow®, Tetric®, and Heliomolar®. Light curable resins could be preferred as light cured resins can be more color stable than chemically cured resins. However, chemical cure or any type of polymerization/hardening/curing of the filling material can also be used. The use of a metallic matrix may dictate the use of a chemical cure. Also, the method is not limited to flowable composite resins with lesser filler particles. One example variation includes an initial placement of a more flowable composite first, which can include flowable composites that are made less viscous than paste composite materials by virtue of lower filler content, but also from thixotropic effect of extrusion thru a small orifice tip, heating of a highly filled paste material that has temporary decreased viscosity to allow more flow and easier placement; or any modification of the paste through chemical and filler content formulation change, temporary or transitional viscosity decrease thru heat, and or pressure and or other physical effect.

A light curable paste composite resin is then extruded onto the flowable composite resin and resin tooth bonding agent without creating air bubbles, allowing the composite resin to displace some of the lesser filled flowable composite resin and resin tooth bonding agent (under magnification if possible). Composite resins are available under tradenames such as 3M Z100™, 3M Filtek Supreme™, and Prodigy®. The next steps are burnishing, carving the anatomy and carving excess composite. There is no need to use a condenser or plugger. Immediately after using the injection molding technique, the matrix moves nicely to close the incisal gap but continues to hug the cervical area of the teeth. The gingival sulcus itself provides stabilization. Alternatively, other products such as silicon stabilizer specific or non specific wedges also can be used with the matrix depending on the specific case or operator preference. Wedges can press the matrix against the root of the tooth. While traditional wedges can smash the exaggerated crown-root junction profile of the matrix, certain wedges may work with delicate stabilization. If a metallic matrix or thick polymeric matrix is used, a traditional wedge will not smash the exaggerated crown-root junction profile of the matrix.

The filled preparation is then cured using a curing light such as high intensity light emitting diode (LED) lights, plasma-arc curing lights, halogen lights, and laser lights. The matrix 30 is then removed, and the restored tooth 12 is polished with discs, strips, and rubber tipped and carbide burs. A seamless filling is achieved.

A diastema can be closed using a single matrix 30 as shown in FIG. 1 or alternatively, two matrices can be used to close a diastema. Turning to FIGS. 2 to 7, there is shown a lower incisor 112 having a clear sectional dental matrix 130 placed on the incisor 112. The dental matrix 130 can be formed from a translucent or transparent material such as a polymeric film. One non-limiting example material is the polyester film commercially available as Mylar™.

Figure 3:
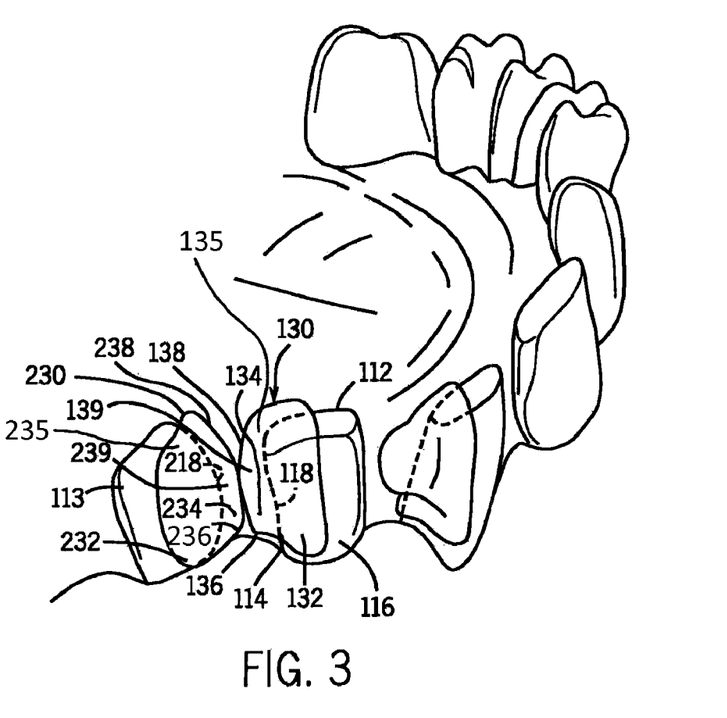
FIG. 3 is a partial top perspective view of the lower human dental arch showing (i) back to back lower incisors, each incisor having a dental matrix according to the invention placed on the incisor, and (ii) another lower incisor having a dental matrix according to the invention placed on the incisor.
Figure 4:
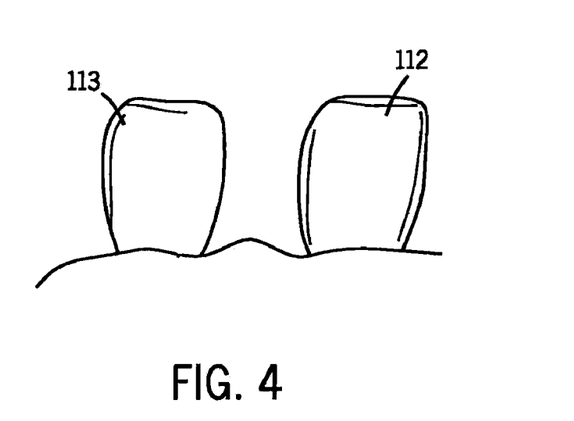
FIG. 4 is a front view of two lower incisors.
Figure 5:
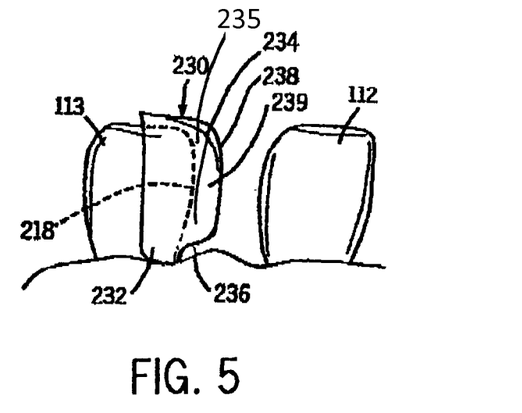
FIG. 5 is a front view of two lower incisors, the incisor on the left of the view having a dental matrix according to the invention placed on the incisor.
Figure 6:
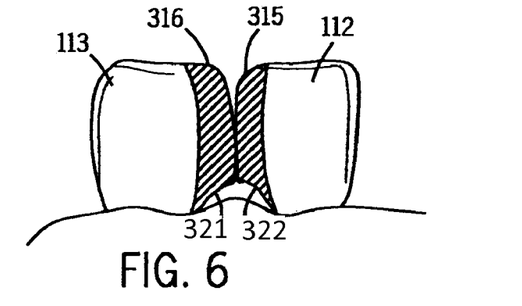
FIG. 6 is a front view of adjacent lower incisors after diastema closure according to the invention.

The matrix 130 has a first root end section 132 that is anatomic in shape. The actual anatomic shapes of the root end section 132 of the matrix 130 can be created from scans of natural teeth, molds of natural teeth, and/or molds of tooth models. Thus, by "anatomic", it is meant that the root end section 132 of the matrix 130 has an inner surface that conforms to the shape of the outer surface of a particular region of the natural tooth that contacts the root end section 132 of the matrix 130. In FIG. 3, the root end section 132 of the matrix 130 conforms to the outer surface 114 of the gingival portion 116 of the tooth 112. The root end section 132 of the matrix 130 can be fully or partially anatomic. As a result, the matrix 130 can be used without interdental wedges or elastic separators or spacers. The anatomic shape allows hands-free and wedge-free use as the matrix 130 hugs the tooth 112.

The sectional matrix 130 has a second (crown root junction profile) section 134 that is integral with the root end section 132. The second section 134 is not anatomically shaped to conform to the shape of the outer surface 118 of the tooth 112. The outer surface 118 may have been created by removal of portions of the tooth 112. Specifically, looking at FIG. 3, an exaggerated root-crown profile 136 of the second section 134 is created at the junction of the root end section 132 and the second section 134. The exaggerated root-crown profile 136 extends away from the outer surface 118 of the tooth 112. The exaggerated root-crown profile 136 merges with a side profile 138 of the second section 134 of the matrix 130. The exaggerated root-crown profile 136 and the side profile 138 of the second section 134 of the matrix 130 create a mild to severe non-anatomic bulge. The space 139 between the outer surface 118 of the tooth 112 and the inner surface of the exaggerated root-crown profile 136 and the side profile 138 creates a mold for the dental filling material that closes the diastema between tooth 112 and tooth 113. The sectional matrix 130 also has a third (incisal) section 135 that is integral with the second section 134. The third section 135 of the matrix 130 can be fully or partially anatomic. The third section 135 of the matrix 130 may comprise about the bottom half of the matrix 130.

The root end section 132 and the third section 135 of the matrix 130 can be tooth specific. By "tooth specific" it is meant that the root end section 132 and the third section 135 of the matrix 130 are configured to conform to the shape of the outer surface of the specific natural tooth being restored, such as (without limitation) a maxillary lateral incisor. The root end section 132 and the third section 135 of the matrix 130 can also be tooth type specific. By "tooth type specific" it is meant that the root end section 132 and the third section 135 of the matrix 130 are configured to conform to the shape of the outer surface of the specific type of natural tooth such as (without limitation) an incisor. The root end section 132 and the third section 135 of the matrix 130 can be tooth surface specific. By "tooth surface specific" it is meant that the root end section 132 and the third section 135 of the matrix 130 are configured to conform to the shape of the outer surface of the specific natural tooth surface such (without limitation) a lingual or buccal incisor surface.

Figure 2:
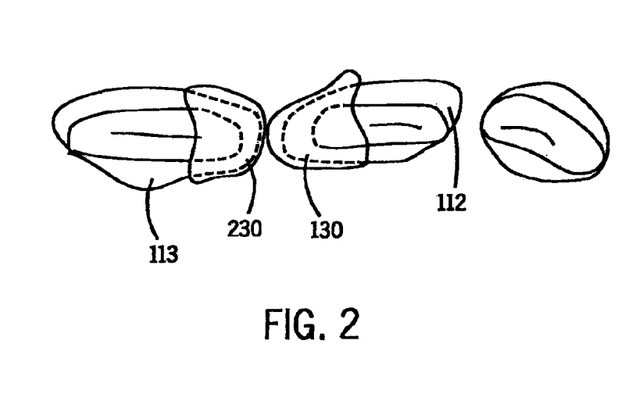
FIG. 2 is a partial top view of the lower human dental arch showing back to back lower incisors, each incisor having a dental matrix according to the invention placed on the incisor.

Still referring to FIGS. 2 and 3, there is shown a lower incisor 113 having a clear sectional dental matrix 230 placed on the incisor 113. The dental matrix 230 can be formed from a translucent or transparent material such as a polymeric film. One non-limiting example material is the polyester film commercially available as Mylar™.

The matrix 230 has a first root end section 232 that is anatomic in shape. The actual anatomic shapes of the root end section 232 of the matrix 230 can be created from scans of natural teeth, molds of natural teeth, and/or molds of tooth models. Thus, by "anatomic", it is meant that the root end section 232 of the matrix 230 has an inner surface that conforms to the shape of the outer surface of a particular region of the natural tooth that contacts the root end section 232 of the matrix 230. In FIG. 3, the root end section 232 of the matrix 230 conforms to the outer surface of the gingival portion of the tooth 113. The root end section 232 of the matrix 230 can be fully or partially anatomic. As a result, the matrix 230 can be used without interdental wedges or elastic separators or spacers. The anatomic shape allows hands-free and wedge-free use as the matrix 230 hugs the tooth 113.

The sectional matrix 230 has a second (crown root junction profile) section 234 that is integral with the root end section 232. The second section 234 is not anatomically shaped to conform to the shape of the outer surface 218 of the tooth 113. The outer surface 218 may have been created by removal of portions of the tooth 113. Specifically, looking at FIG. 3, an exaggerated root-crown profile 236 of the second section 234 is created at the junction of the root end section 232 and the second section 234. The exaggerated root-crown profile 236 extends away from the outer surface 218 of the tooth 113. The exaggerated root-crown profile 236 merges with a side profile 238 of the second section 234 of the matrix 230. The exaggerated root-crown profile 236 and the side profile 238 of the second section 234 of the matrix 230 create a mild to severe non-anatomic bulge. The space 239 between the outer surface 218 of the tooth 113 and the inner surface of the exaggerated root-crown profile 236 and the side profile 238 creates a mold for the dental filling material that closes the diastema between tooth 112 and tooth 113. The sectional matrix 230 also has a third (incisal) section 235 that is integral with the second section 234. The third section 235 of the matrix 230 can be fully or partially anatomic. The third section 235 of the matrix 230 may comprise about the bottom half of the matrix 230.

The root end section 232 and the third section 235 of the matrix 230 can be tooth specific. By "tooth specific" it is meant that the root end section 232 and the third section 235 of the matrix 230 are configured to conform to the shape of the outer surface of the specific natural tooth being restored, such as (without limitation) a maxillary lateral incisor. The root end section 232 and the third section 235 of the matrix 230 can also be tooth type specific. By "tooth type specific" it is meant that the root end section 232 and the third section 235 of the matrix 230 are configured to conform to the shape of the outer surface of the specific type of natural tooth such as (without limitation) an incisor. The root end section 232 and the third section 235 of the matrix 230 can be tooth surface specific. By "tooth surface specific" it is meant that the root end section 232 and the third section 235 of the matrix 230 are configured to conform to the shape of the outer surface of the specific natural tooth surface such (without limitation) a lingual or buccal incisor surface.

Figure 7:
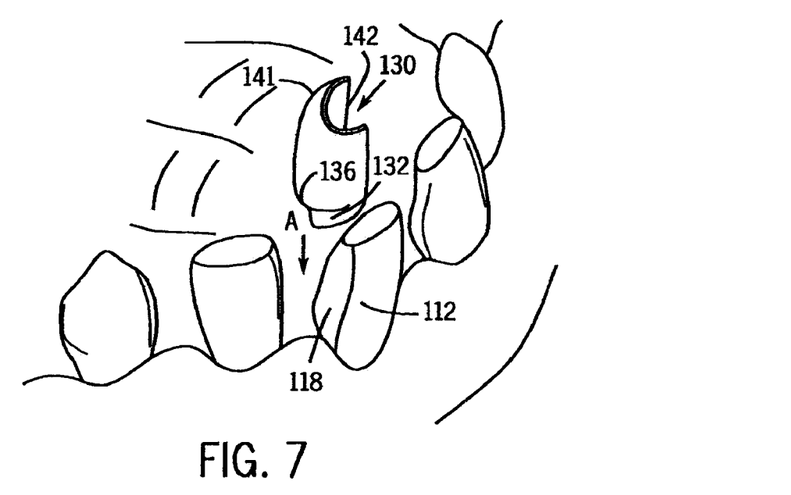
FIG. 7 is a top perspective view of the matrix insertion step of the method according to the invention.

Looking at FIG. 7, the clear plastic sectional matrix 130 is placed downward (see Arrow A) around the tooth 112 and maintains anatomic root adaptation contact by way of the anatomic root end section 132 of the matrix 130. Likewise, the clear plastic sectional matrix 230 is placed around the tooth 113 and maintains anatomic root adaptation contact by way of the anatomic root end section 232 of the matrix 230 (see FIG. 5). The outer surface 118 of tooth 112 is then etched with liquid and/or gel phosphoric acid. The outer surface 118 of tooth 112 can be reached by way of a slit 142 in the end 141 of the matrix 130, or by gently pulling the incisal portion of the matrix 30 away from the tooth while leaving the gingival portion of the matrix 130 undisturbed. Similarly, the outer surface 218 of tooth 113 is then etched with liquid and/or gel phosphoric acid. The outer surfaces 118 and 218 of teeth 112, 113 are then rinsed and dried. A lightly filled or unfilled light curable resin tooth bonding agent is then applied to the outer surfaces 118 and 218 of teeth 112, 113. The resin tooth bonding agent is not light cured at this point.

A light curable flowable composite resin is then injected directly on the resin tooth bonding agent (under magnification if possible) without incorporating bubbles. A tiny amount of the light curable flowable composite resin is expressed before placement to ensure that there is no air in the cannula. The light curable flowable composite and resin tooth bonding agent are not light cured at this point. A light curable paste composite resin is then extruded onto the flowable composite resin and resin tooth bonding agent without creating air bubbles, allowing the composite resin to displace some of the lesser filled flowable composite resin and resin tooth bonding agent (under magnification if possible). The next steps are burnishing, carving the anatomy and carving excess composite. There is no need to use a condenser or plugger. The filled preparations are then cured using a curing light such as high intensity light emitting diode (LED) lights, plasma-arc curing lights, halogen lights, and laser lights. The matrix 130 and the matrix 230 are then removed, and the restored teeth 112 and 113 are polished with discs, strips, and rubber tipped and carbide burs. Looking at FIG. 6, the diastema between teeth 112 and 113 has been closed by filling 315 and filling 316. Note the bottom edges 321, 322 formed by the exaggerated root-crown profiles 136, 236 of the sectional matrix 130, 230. The bottom edges 321, 322 of the fillings 315, 316 provide space for the interdental papilla.

An example restorative treatment according to the invention can also be used for papilla regeneration. This demonstrates an important principle, i.e., any restorative procedure involving the interproximal area is a candidate for papilla regeneration. This example can be described with reference to FIGS. 8-18 and Table 1.

TABLE 1

Case Study
Clinical steps for combined papilla regeneration and/or diastema closure 1. Teeth are aggressively cleaned with rubber cup and flour of pumice.
2. Interproximal areas are aggressively sprayed with high pressure sodium bicarbonate. Rubber dam placement is not mandatory but is helpful.
3. If defective restorations are present, the affected areas are re-prepared with "saucer shaped" cavity preparations. Infinity edge margins are created with coarse and fine diamonds. Thus, the preparations are not "beveled" per se, instead the correct description is a "saucer" shape with and infinity edge margin.
4. Diastema closure matrices are placed.
5. Total etch technique is utilized.
6. Bonding resin is placed but not light cured.
7. Flowable composite is injected into the cervical area, and then light cured.
8. Tooth separation is then created with a wedge.
9. Bonding resin is placed followed with a small amount of flowable composite then followed with paste composite placement.
10. Light curing all three components of step 9 together.
11. Sculpting and polishing. Final polish with new diamond impregnated polisher.
12. High level magnification throughout the procedure is recommended.

Note:
for strict papilla regeneration, steps 3, 6, 7, and 8 are eliminated as the contact area of the affected teeth is already present.

A case study for the combined papilla regeneration and diastema closure follow. A patient originally presented with failing silicate restorations on the mesial of the upper right lateral incisor and the distal of the right central incisor. The patient requested that only the one interproximal area be treated, and that the right canine-lateral area could be restored subsequently. Local anesthetic was administered and rubber dam placed.

Figure 8:
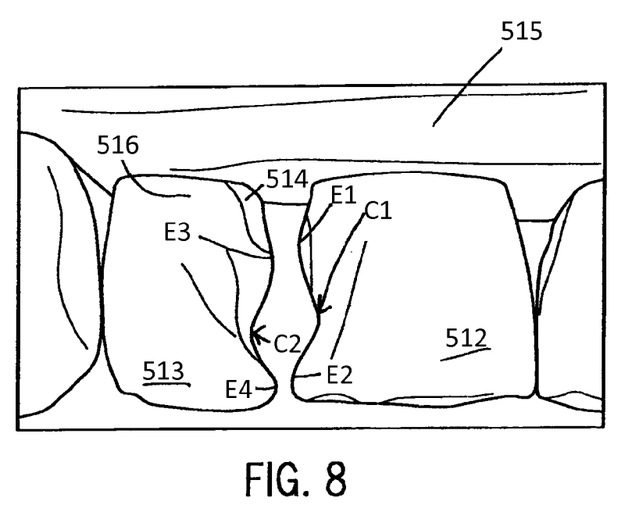
FIG. 8 is a facial view of two incisors having opposed "saucer" shape cavity preparations with infinity edge margins.

FIG. 8 shows teeth 512, 513 in which modern non retentive composite preparations C1 and C2 have been prepared. The cavity preparations C1, C2 are "saucer shaped" and have infinity edge margins E1, E2 and E3, E4. A rubber dam 515 has been placed.

Figure 9:
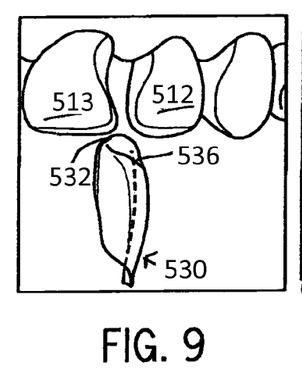
FIG. 9 is a facial view of the matrix insertion step of the method according to the invention.
Figure 10:
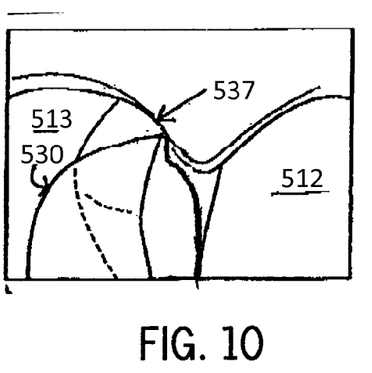
FIG. 10 shows a root end section of the matrix of FIG. 9 as the matrix slides into the gingival sulcus.
Figure 11:
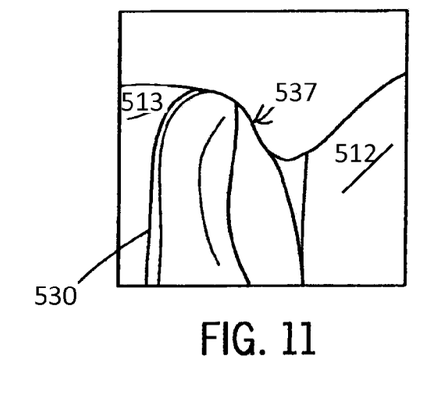
FIG. 11 shows a root end section of the matrix of FIGS. 9 and 10 as the matrix is engaged by the interdental papilla. The papilla stabilizes the matrix, and the matrix in turn "squeezes" the papilla.

A dental matrix 530 according to the invention is shown being placed in FIGS. 9-11. The diastema closure matrix 530 allows a smooth yet aggressive cervical curvature 536 that facilitates direct composite architectures that are extremely conducive to papilla regeneration. This is due to two inherent features. The first feature is the ability to forgo a traditional dental wedge, and to use the papilla as a wedging force. A traditional dental wedge would have created a flat cervical shape. Flat cervical shapes lack the static pressure needed to regenerate papillae. The second feature is a complete anatomic shape that permits the clinician to simply remove the matrix 530 after photo polymerization with little to no interproximal finishing. The matrix 530 has an aggressive cervical curvature 536 which transitions abruptly to a root end section 532 that is anatomic in shape. The root end section 532 of the matrix 530 conforms to the outer surface 514 of the gingival portion 516 of the tooth 513. As a result, the matrix 530 can be used without interdental wedges or elastic separators or spacers. As the matrix 530 slides into the gingival sulcus 537, the papilla is engaged. The papilla stabilizes the matrix 530, and the matrix 530 in turn "squeezes" the papilla. A second matrix 630 having similar features to matrix 530 can be placed on tooth 512.

When the finish of the cured composite material is extremely smooth and there is a lack of a gingival ledge, tissue health can be ideal, even with very round embrasure form. This modern view of cervical curvature is in sharp contrast to the outdated notion that prosthetic and restorative embrasures should be flat.

Figure 12:
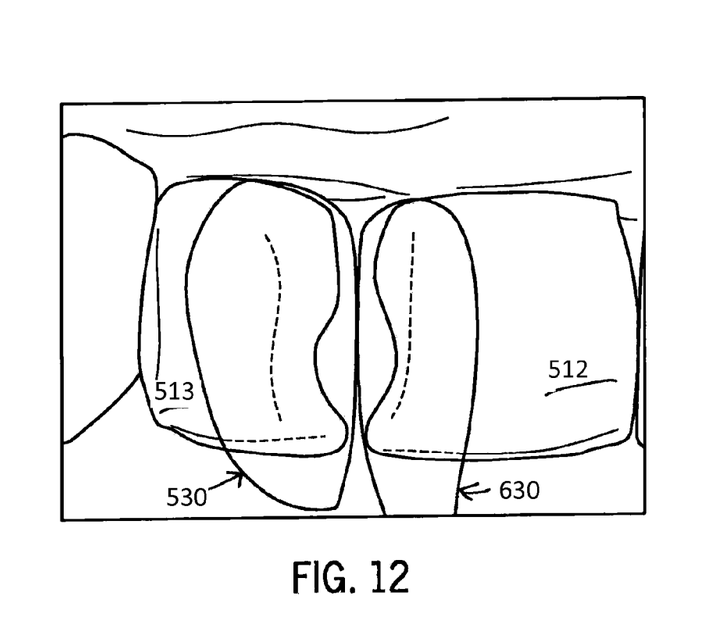
FIG. 12 shows a facial view of back to back matrices with the gingival edge of each matrix three millimeters sub-gingival.
Figure 13:
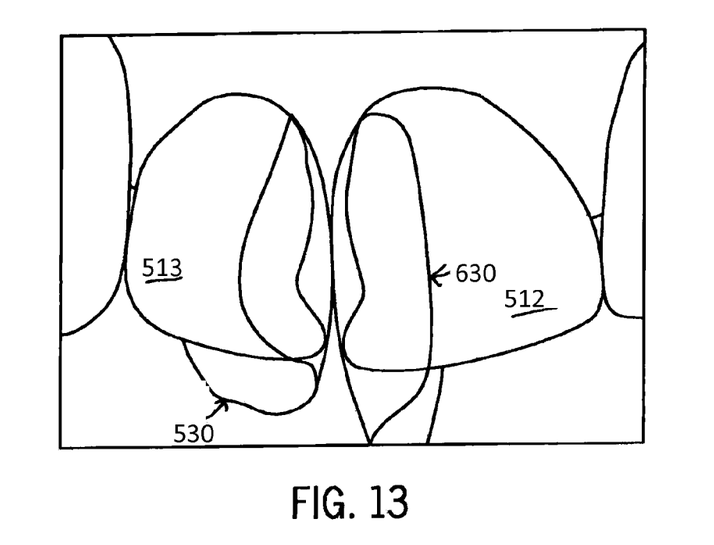
FIG. 13 shows a palatal view of back to back matrices of FIG. 12.
Figure 14:
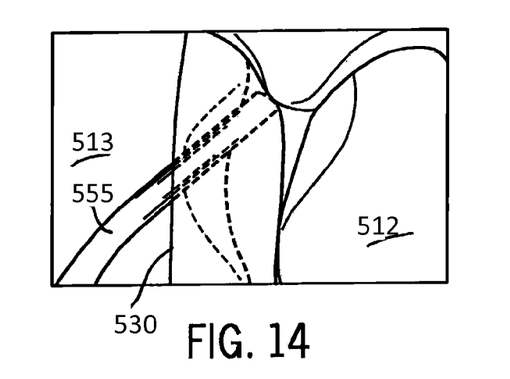
FIG. 14 shows a facial view of an initial increment of flowable composite being injected between the tooth and the matrix.
Figure 15:
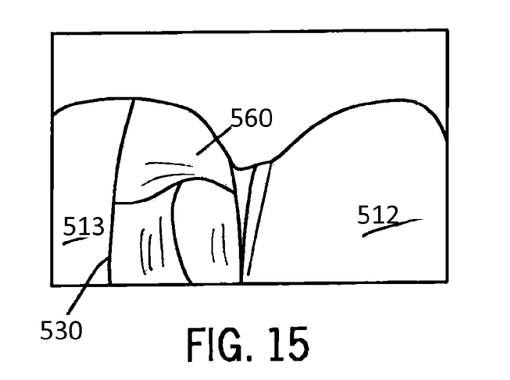
FIG. 15 shows a facial view of a two millimeter increment of flowable composite having been placed and photo-polymerized.
Figure 16:
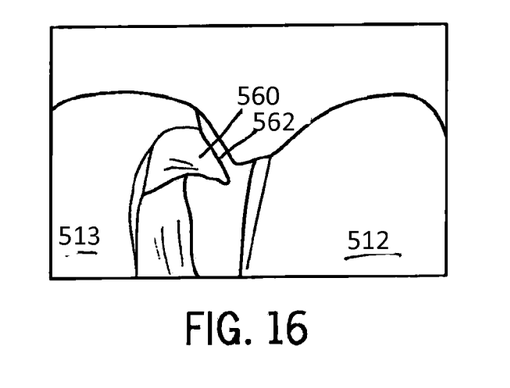
FIG. 16 shows a facial view of the cervical shape and impeccable marginal integrity of the composite increment of FIG. 15 after the matrix is removed.

The case continues with both of the matrices 530, 630 in position (see FIGS. 12-13). Total etch remains as the most robust method when bonding to large enamel areas, especially on uncut enamel There is no need to stabilize the matrices 530, 630 as their design makes them self-stabilizing. After placing a bonding agent (such as one described above), an initial small increment of flowable composite (such as one described above) is carefully injected via tip 555 to both teeth to fill this crucial cervical area (see FIG. 14) (light curing is not pictured). Advanced magnification is advantageous for this step. Advanced magnification is beneficial for optimal soft tissue response. Flowable composite rather than paste composite is preferred for this first increment. Paste composite could be difficult to place in this cervical area without voids and without disturbing the matrices 530, 630. The flowable composite is cured creating a cervical undercut 560 shown in FIG. 15 (with matrix 530 in place) and FIG. 16 (with matrix 530 removed for clarity). Note the smooth surface 562 which is formed in the cervical curvature 536 of the matrix 530 such that there is a lack of a gingival ledge in the cervical undercut 560. A similar cervical undercut 660 is created on tooth 512 using the same technique.

Figure 17:
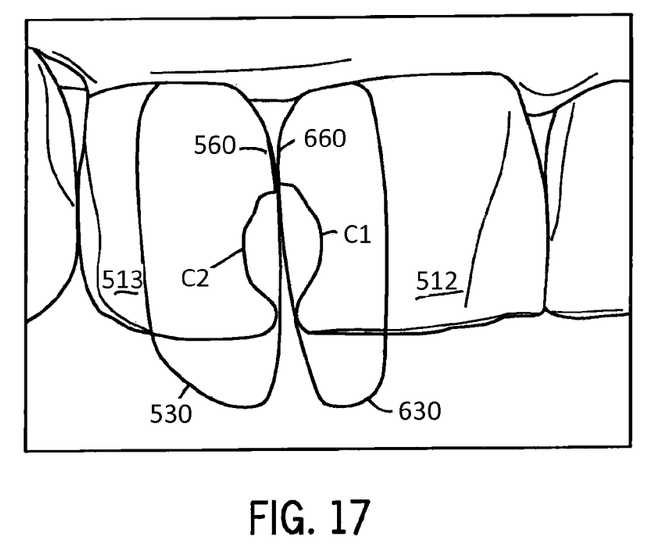
FIG. 17 shows a facial view of back to back matrices in place after a two millimeter increment of flowable composite has been placed and photo-polymerized.
Figure 18:
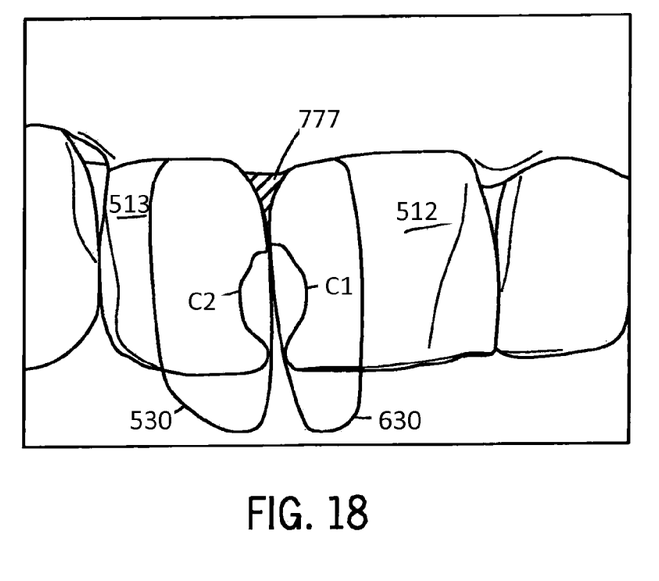
FIG. 18 shows a facial view of a wedge (shown in cross-section) inserted to gain tooth separation to compensate for the matrix thicknesses. A soft silicone wedge is used because it will not elicit the patient discomfort typical of a traditional wedge as it presses the palatal tissue.

Once cervical undercuts 560, 660 are established for teeth 512, 513 as shown in FIG. 17, a dental wedge 777 (shown in cross-section in FIG. 18) is placed to separate the teeth 512, 513 enough to compensate for the thickness of the matrices 530, 630. Otherwise, when the matrices 530, 630 are removed the contact may be open. Bonding resin (such as one described above) is placed in the matrices 530, 630 to fill cavity preparations C1, C2, followed with a small amount of flowable composite (such as one described above) then followed with placement paste composite (such as one described above). The bonding resin, the flowable composite, and the paste composite are light cured together. Once the matrices 530, 630 are removed, the teeth 512, 513 spring back to establish a snug contact. Once the matrices 530, 630 are removed, the smooth and extremely durable surface is visible. This achieves the goal of composite dentistry to do little or preferably no interproximal finishing. That is because a "matrix composite finish" has no oxygen inhibited layer. Microscope studies of extracted teeth show that an undisturbed interproximal matrix finish stays mirror smooth for years, even decades. Conversely interproximal areas which were "polished" by the dentist are often gouged, rough and stained.

Differently dimensioned matrices can be provided in a diastema closure kit. For example, a first smaller size upper incisor anatomic matrix can be included in the diastema closure kit. A second medium size diastema closure universal upper incisor matrix such as matrix 530 can be included in the diastema closure kit. The second size diastema closure is suitable for most diastema closures. A third larger size extreme diastema closure universal upper incisor can be included in the diastema closure kit. The third size, such as matrix 230, has a very aggressive cervical curvature (such as 236 in FIG. 5) for extreme diastema closure cases. While the example kit has three different size matrices, the kit can include any number of different size matrices.

Various rules of thumb for space closure can be associated with these three sizes of matrix in the example kit. For example, for a ½ millimeter space between teeth, the first size may be selected by the dentist. For a 1 millimeter space between teeth, the second size may be selected by the dentist. For a space between teeth of 2 millimeters or more, the third size may be selected by the dentist. For a mild diastema closure (½ mm.), gingival diastemas will close very nicely with the first size matrix. For a moderate diastema closure (1 mm.), the dentist can use one of the second size matrix, and if restoring adjacent teeth, (say the mesial of #8 and the mesial of #9), the dentist can use two of the first size matrix. In certain circumstances, a full 1 millimeter gap can be closed unilaterally, because the tooth form of a tooth (such as a peg lateral) can require that all of the composite be added to one tooth only. If a dentist is restoring both teeth approximating the diastema, then the dentist needs to calculate a doubling of the closing capabilities for the above mentioned spaces, and reduce the level of gingival curvature in matrix selection from the kit. For example, for a 1 millimeter space, a dentist may use one of the second size matrix, or two of the first size matrix. For severe diastema closures, the dentist can use the third size matrix, or two of the third size matrix.

Because gingiva adapts to a wide range of shapes, clinicians can now create convenient interproximal shapes if the restorations are smooth and without a sharp marginal ledge. Bridge abutments and exotic implant emergence profiles have aptly demonstrated this clinical reality. Restoratively driven papilla regeneration according to the invention should become a viable option for all restorative dentists. Until now there were very few dedicated tools or techniques for restoratively driven papilla regeneration. Previous attempts at both diastema closure and papilla regeneration using direct composites often ended with significant compromise in periodontal health. The interdental papilla serves as both an esthetic and functional asset, and anatomically ideal interproximal composite shapes formed using the methods of the invention can serve as a predictable scaffold to regain this valuable gingival architecture.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:
1. A dental matrix for diastema closure comprising:
a curved strip of translucent material, the strip having a length from a first end to a second end sufficient to create a form for molding a restorative material to a surface of a tooth to be restored, the strip having a root end section and a second section that connects with the root end section at a root crown junction,
wherein the root end section of the strip is for insertion into the sulcus between the papilla and the gingival portion of the tooth to be restored and is anatomic in shape for conforming to the outer surface of the gingival portion of the tooth to be restored, and wherein the matrix forms a convex inner surface at the root crown junction that extends into the second section thereby forming an outward bulbous bulge for positioning along the gum line of the tooth to be restored for the closure of the diastema.

2. The dental matrix of claim 1 wherein:
the root end section is dimensioned such that the root end section can engage papilla and a gingival portion of the tooth when the root end section is inserted into the sulcus between the papilla and the gingival portion of the tooth.

3. The dental matrix of claim 1 wherein:
the second section extends outwardly away from a root-crown junction of the root end section and the second section.

4. The dental matrix of claim 1 wherein:
the second section extends outwardly away from a root-crown junction of the root end section and the second section such that a curved profile is formed in the second section adjacent the root-crown junction.

5. The dental matrix of claim 1 wherein:
the root end section has a vertical dimension in the range of 0.5 to 2 millimeters.

6. The dental matrix of claim 1 wherein:
the strip includes a third section integral with the second section, the root end section and the third section being on opposite sides of the second section.

7. The dental matrix of claim 6 wherein:
the root end section of the strip and/or the third section of the strip are tooth specific.

8. The dental matrix of claim 1 wherein:
the root end section of the strip is specific to an anterior tooth.

9. The dental matrix of claim 1 wherein:
the root end section of the strip and/or the third section of the strip are tooth type specific.

10. The dental matrix of claim 1 wherein:
the root end section of the strip and/or the third section of the strip are tooth surface specific.

11. The dental matrix of claim 1 wherein:
the strip is dimensioned such that the dental matrix is suitable for use without an interdental wedge or an elastic separator or a spacer.

12. A method for closing a diastema between a first tooth and a second tooth, the method comprising:
providing a dental matrix comprising a curved sectional strip of material, the strip having a length from a first end to a second end sufficient to create a form for molding a restorative material to a surface of the first tooth, the strip having a root end section and a second section that connects with the root end section at a root crown junction wherein the root end section of the strip is for insertion into the sulcus between the papilla and the gingival portion of the first tooth and is anatomic in shape for conforming to the outer surface of the gingival portion of the first tooth, wherein the matrix forms a convex inner surface at the root crown junction that extends into the second section thereby forming an outward bulbous bulge for positioning along the gum line of the first tooth for the closure of the diastema;
inserting the root end section of the dental matrix into the sulcus between the papilla and the gingival portion of the first tooth such that the bulge is positioned in a cervical area between the first tooth and the second tooth;
placing a composite restorative material in the cervical area between the dental matrix and a cervical surface of the first tooth; and
thereafter curing the composite restorative material.

13. The method of claim 12 wherein:
a surface of the cured composite restorative material bonded to the cervical surface of the first tooth is curved.

14. The method of claim 12 further comprising:
thereafter placing a second composite restorative material between the dental matrix and an interproximal surface of the first tooth; and
thereafter curing the second composite restorative material.

15. The method of claim 12 further comprising:
placing a wedge between the first tooth and the second tooth;
thereafter placing a second composite restorative material between the dental matrix and an interproximal surface of the first tooth; and
thereafter curing the second composite restorative material.

16. The method of claim 12 further comprising:
providing a second dental matrix comprising a curved sectional strip of material, the strip of the second dental matrix having a length from a first end to a second end sufficient to create a form for molding a restorative material to a surface of the second tooth, the strip of the second dental matrix having a root end section and a second section integral with the root end section of the second dental matrix wherein the root end section of the strip of the second dental matrix is anatomic in shape;
inserting the root end section of the second dental matrix into the sulcus between the papilla and the gingival portion of the second tooth;
placing a second composite restorative material between the second dental matrix and a cervical surface of the second tooth; and
thereafter curing the second composite restorative material.

17. A method for regenerating papilla between a first tooth and a second tooth, the method comprising:
providing a dental matrix comprising a curved sectional strip of material, the strip having a length from a first end to a second end sufficient to create a form for molding a restorative material to a surface of the first tooth, the strip having a root end section and a second section that connects integral with the root end section at a root crown junction wherein the root end section of the strip is for insertion into the sulcus between the papilla and the gingival portion of the first tooth and is anatomic in shape for conforming to the outer surface of the gingival portion of the first tooth, wherein the matrix forms a convex inner surface at the root crown junction that extends into the second section thereby forming an outward bulbous bulge for positioning along the gum line of the first tooth for regenerating papilla;
inserting the root end section of the dental matrix into the sulcus between the papilla and the gingival portion of the first tooth such that the bulge is positioned in a cervical area between the first tooth and the second tooth;
placing a composite restorative material in the cervical area between the dental matrix and a cervical surface of the first tooth; and
thereafter curing the composite restorative material.

18. The method of claim 17 further comprising:
providing a second dental matrix comprising a curved sectional strip of material, the strip of the second dental matrix having a length from a first end to a second end sufficient to create a form for molding a restorative material to a surface of the second tooth, the strip of the second dental matrix having a root end section and a second section integral with the root end section of the second dental matrix wherein the root end section of the strip of the second dental matrix is anatomic in shape;

inserting the root end section of the second dental matrix into the sulcus between the papilla and the gingival portion of the second tooth;

placing a second composite restorative material between the second dental matrix and a cervical surface of the second tooth; and thereafter curing the second composite restorative material.

* * * * *